(12) United States Patent
Barnett et al.

(10) Patent No.: US 6,733,972 B2
(45) Date of Patent: May 11, 2004

(54) DETECTION OF MYCOSPHAERELLA USING THE POLYMERASE CHAIN REACTION

(75) Inventors: Charles Jason Barnett, Carrboro, NC (US); James Joseph Beck, Morrisville, NC (US)

(73) Assignee: Syngenta Participations AG, Basel (CH)

( * ) Notice: Subject to any disclaimer, the term of this patent is extended or adjusted under 35 U.S.C. 154(b) by 184 days.

(21) Appl. No.: 09/961,663

(22) Filed: Sep. 24, 2001

(65) Prior Publication Data

US 2002/0115084 A1 Aug. 22, 2002

Related U.S. Application Data

(63) Continuation of application No. PCT/EP01/06783, filed on Jun. 15, 2001.
(60) Provisional application No. 60/211,902, filed on Jun. 16, 2000.

(51) Int. Cl.$^7$ ............... C12Q 1/68; C12P 19/34; C07H 21/04
(52) U.S. Cl. ............... 435/6; 435/91.2; 536/23.1; 536/24.3
(58) Field of Search ............... 435/6, 91.1, 91.2; 536/23.1, 24.3

(56) References Cited

U.S. PATENT DOCUMENTS

| | | |
|---|---|---|
| 4,683,195 A | 7/1987 | Mullis et al. ............ 435/6 |
| 4,683,202 A | 7/1987 | Mullis ............ 435/91 |
| 5,585,238 A | * 12/1996 | Ligon et al. ............ 435/6 |
| 5,800,997 A | 9/1998 | Beck ............ 435/6 |
| 5,955,274 A | 9/1999 | Ligon et al. ............ 435/6 |

FOREIGN PATENT DOCUMENTS

| EP | 0 955 381 A2 | 11/1999 | ............ C12Q/1/68 |
|---|---|---|---|

OTHER PUBLICATIONS

Genbank accession No. AF173311: Jan. 25, 2000.*

Carlier, J. et al. *Septoria leaf Spot of Banana: A Newly Discovered Disease Caused by Mycosphaerella eumusae (Anamorph Septoria eumusae) Phytopathology*, vol. 90, No. 8 (Aug. 2000), pp. 884–890.

Johanson, A., "PCR for Detection of the Fungi that Cause Sigatoka Leaf Spots of Banana and Plaintain," In: eds. Schots, et al., *Modern Assays for Plant Pathogenic Fungi: Identification, Detection and Quantification* (CAB International, 1994), pp. 215–221.

Johanson, A, et al. *The use of species–specific DNA probes for the identification of Mycosphaerella fijiensis and M. musicola, the causal agents of Sigatoka disease of banana Plant Pathology*, vol. 43 (1994), pp. 701–707.

Nazar, et al. *Potential use of PCR–amplified ribosomal intergenic sequences in the detection and differentiation of verticillium wilt pathogens Physiological and Molecular Plant Pathology*, vol. 39, (1991), pp. 1–11.

Romero, R.A. and Sutton, T.B. *Sensitivity of Mycosphaerella fijiensis, Causal Agent of Black Sigatoka of Banana, to Propiconazole Phytopathology*, vol. 87, No. 1 (Jan. 1997), pp. 96–100.

Beck, J. J. and Ligon, J.M., *Polymerase Chain Reaction Assays for the Detection of Stagonospora nodorum and Septoria tritici in Wheat The American Phytopathological Society*, vol. 85, No. 3 (1995), pp. 319–324.

Crous et al, *Uwebraunia and Dissoconium, two morphologically similar anamorph genera with distinct teleomorph affinity* Genbank Accession No. AF173311 [online], [retrieved on Sep. 19, 2002]. Retrieved from NCBI/GENBANK (gi: 6746416): <URL: http://www.ncbi.nlm.nih.gov/>.

Ligon et al, *Detection of Fungal Pathogens Using the Polymerase Chain Reaction Biotechnology Advances*, Elsevier Publishing, Barking, GB, vol. 15, No. 3–4, (1997) pp. 698.

Stewart et al, *Phylogenetic relationships among some cercosporoid anamorphs of Mycosphaerella based on rDNA sequence analysis Mycological Research*, vol. 103 (11), (1999) pp. 1491–1499.

* cited by examiner

*Primary Examiner*—Jehanne S. Sitton
(74) *Attorney, Agent, or Firm*—Mary Kakefuda

(57) ABSTRACT

The present invention relates to the use of primers in polymerase chain reaction assays for the detection of a fungal pathogen of banana, a heretofore unknown species of Mycosphaerella. Specific primers are identified as being useful for the identification of fungal isolates using PCR based techniques.

3 Claims, No Drawings

```
                              SEQUENCE LISTING

<160> NUMBER OF SEQ ID NOS: 19

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer ITS1

<400> SEQUENCE: 1
tccgtaggtg aacctgcgg                                                    19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer ITS2

<400> SEQUENCE: 2
gctgcgttct tcatcgatgc                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer ITS3

<400> SEQUENCE: 3
gcatcgatga agaacgcagc                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer ITS4

<400> SEQUENCE: 4
tcctccgctt attgatatgc                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer
```

```
           J-BP1

<400> SEQUENCE: 5
gcatcattgc gtcggagtaa                                           20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer
      J-BP2

<400> SEQUENCE: 6
tcattgcgtc ggagtaaaag t                                         21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer
      J-BP3

<400> SEQUENCE: 7
tcattgcgtc ggagtaaaag t                                         21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer
      J-BP4

<400> SEQUENCE: 8
cattgcgtcg gagtaaaagt ga                                        22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer
      J-BP5

<400> SEQUENCE: 9
gcgtcggagt aaaagtgaat ga                                        22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer
      J-BP6

<400> SEQUENCE: 10
gcctccgaag cgaatagttg                                           20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer
      J-BP7
```

<400> SEQUENCE: 11
ggcctccgaa gcgaatagtt                                                    20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer
      J-BP8

<400> SEQUENCE: 12
cctccgaagc gaatagtt                                                      18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Primer
      JB-473

<400> SEQUENCE: 13
ggcctccgaa gcgaatag                                                      18

<210> SEQ ID NO 14
<211> LENGTH: 377
<212> TYPE: DNA
<213> ORGANISM: Mycosphaerella sp.
<220> FEATURE:
<221> NAME/KEY: misc_feature
<222> LOCATION: (1)..(377)
<223> OTHER INFORMATION: Truncated DNA sequence for the Internal
      Transcribed Spacer of a fungus amplified from
      banana sample "Capesterre-babin 2".

<400> SEQUENCE: 14
acactgcatc attgcgtcgg agtaaaagtg aatgaaacaa aactttcaac aacggatctc        60
ttggttccag catcgatgaa gaacgcagcg aaatgcgata agtaatgtga attgcagaat       120
tcagtgaatc atcgaatctt tgaacgcaca ttgcgccctc tggtattccg gggggcatgc       180
ctgttcgagc gtcatttcac cactcaagcc tggcttggta ttgggcgtcg cggtaccgcg       240
cgccttaaag tcttccggct gagctgtccg tctctaagcg ttgtggcaac tattcgcttc       300
ggaggccggg cggccgcggc cgttaaatct ttcacaaggt tgacctcgga tcaggtaggg       360
atacccgctg aacttaa                                                     377

<210> SEQ ID NO 15
<211> LENGTH: 377
<212> TYPE: DNA
<213> ORGANISM: Mycosphaerella sp.
<220> FEATURE:
<221> NAME/KEY: misc_feature
<222> LOCATION: (1)..(377)
<223> OTHER INFORMATION: Truncated DNA sequence for the Internal
      Transcribed Spacer of fungus amplified from banana
      sample "Matouba bas 3"

<400> SEQUENCE: 15
acactgcatc attgcgtcgg agtaaaagta aatgaaacaa aactttcaac aacggatctc        60
ttggttccag catcgatgaa gaacgcagcg aaatgcgata agtaatgtga attgcagaat       120
tcagtgaatc atcgaatctt tgaacgcaca ttgcgccctc tggtattccg gggggcatgc       180

-continued

```
ctgttcgagc gtcatttcac cactcaagcc tggcttggta ttgggcgtcg cggtgccgcg    240
cgccttaaag tcttccggct gagctgtccg tctctaagcg ttgtggcaac tattcgcttc    300
ggaggccggg cggccgcggc cgttaaatct ttcacaaggt tgacctcgga tcaggtaggg    360
atacccgctg aacttaa                                                   377
```

<210> SEQ ID NO 16
<211> LENGTH: 377
<212> TYPE: DNA
<213> ORGANISM: Mycosphaerella sp.
<220> FEATURE:
<221> NAME/KEY: misc_feature
<222> LOCATION: (1)..(377)
<223> OTHER INFORMATION: Truncated DNA sequence for the Internal
      Transcribed Spacer of a fungus amplified from
      banana sample "Temoin Infest Forte"

<400> SEQUENCE: 16

```
acactgcatc attgcgtcgg agtaaaagta atgaaacaa aactttcaac aacggatctc     60
ttggttccag catcgatgaa gaacgcagcg aaatgcgata agtaatgtga attgcagaat   120
tcagtgaatc atcgaatctt tgaacgcaca ttgcgccctc tggtattccg ggggggcatgc  180 ctgttcgagc gtcatttcac cactcaagcc tggcttggta ttgggcgtcg cggtgccgcg   240
cgccttaaag tcttccggct gagctgtccg tctctaagcg ttgtggcaac tattcgcttc   300
ggaggccggg cggccgcggc cgttaaatct ttcacaaggt tgacctcgga tcaggtaggg   360
atacccgctg aacttaa                                                   377
```

<210> SEQ ID NO 17
<211> LENGTH: 534
<212> TYPE: DNA
<213> ORGANISM: Mycosphaerella fijiensis

<400> SEQUENCE: 17

```
tccgtaggtg aacctgcgga gggatcatta ccgagtgagg gctcacgccc gacctccaac    60
cctttgtgaa ccacaacttg ttgcttcggg ggcgacctgc cgtcggcggg cgccccgga   120 ggccgtctaa acactgcatc tttgcgtcgg agtttaaaac aaatcgaaca aaactttcaa  180
caacggatct cttggttctg gcatcgatga agaacgcagc gaaatgcgat aagtaatgtg   240
aattgcagaa ttcagtgaat catcgaatct tgaacgcac attgcgccct tggtattcc    300 gaagggcatg cctgttcgag cgtcatttca ccactcaagc ctggcttggt attgggcgtc   360
gcggttcttc gcgcgcctta aagtctccgg ctgagctgtc cgtctctaag cgttgtggat   420
ctttcaattc gcttcggagt gcgggtggcc gcggccgtta atctttatt caaaggttga    480 cctcggatca ggtagggata cccgctgaac ttaagcatat caataagcgg agga          534
```

<210> SEQ ID NO 18
<211> LENGTH: 540
<212> TYPE: DNA
<213> ORGANISM: Mycosphaerella musicola

<400> SEQUENCE: 18

```
tccgtaggtg aacctgcggg gggatcatta ccgagtgagg gctcaccccc gacctccaac    60
cctttgtgaa ccacacctgt tgcttcgggg gcgaccctgc cggcgaactt gtcgccgggc   120
gcccccggag gtctccttaa cactgcatct ctgcgtcgga gttccaaaca aatcggacaa  180
aactttcaac aacggatctc ttggttctgg catcgatgaa gaacgcagcg aaatgcgata   240
agtaatgtga attgcagaat tcagtgaatc atcgaatctt tgaacgcaca ttgcgccctt   300
```

```
tggcattccg aagggcatgc ctgttcgagc gtcatttcac cactcaagcc tagcttggta      360
ttgggcgccg cggtgctccg cgcgccccaa agtctcccgg ctaagccgtc cgtctctaag      420
cgttgtggat ttttcagttc gctccggagc gcgggtggcc gcggccgtta aatcttcaaa      480
ggttgacctc ggatcaggta gggatacccg ctgaacttaa gcatatcaat aagcggagga      540
```

<210> SEQ ID NO 19
<211> LENGTH: 377
<212> TYPE: DNA
<213> ORGANISM: Artificial Sequence
<220> FEATURE:
<223> OTHER INFORMATION: Description of Artificial Sequence: Consensus
      sequence of Mycosphaerella sp. ITS sequences shown
      in SEQ ID NO:14-16.

<400> SEQUENCE: 19

```
acactgcatc attgcgtcgg agtaaaagta aatgaaacaa aactttcaac aacggatctc       60
ttggttccag catcgatgaa gaacgcagcg aaatgcgata agtaatgtga attgcagaat      120
tcagtgaatc atcgaatctt tgaacgcaca ttgcgccctc tggtattccg gggggcatgc      180
ctgttcgagc gtcatttcac cactcaagcc tggcttggta ttgggcgtcg cggtgccgcg      240
cgccttaaag tcttccggct gagctgtccg tctctaagcg ttgtggcaac tattcgcttc      300
ggaggccggg cggccgcggc cgttaaatct ttcacaaggt tgacctcgga tcaggtaggg      360
atacccgctg aacttaa                                                    377
```

US 6,733,972 B2

DETECTION OF MYCOSPHAERELLA USING THE POLYMERASE CHAIN REACTION

This application claims the benefit of U.S. Provisional Patent Application No. 60/211,902, filed Jun. 16, 2000, and is a continuation of International Application No. PCT/EP01/06783, filed Jun. 15, 2001, each of which is incorporated herein in their entireties by reference.

FIELD OF THE INVENTION

The present invention relates to the use of primers in polymerase chain reaction assays for the detection of a heretofore unknown species of the banana pathogen Mycosphaerella. The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; Seed Sci. & Technol. 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; Proc. 1981 Brit. Crop Prot. Conf.) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and Mycosphaerella fijiensis to triazoles to mention just a few (Jones and Clifford; Cereal Diseases, John Wiley, 1983).

There are two well-known forms of sigatoka leaf spots which affect bananas—yellow sigatoka, caused by Mycosphaerella musicola and black sigatoka caused by Mycosphaerella fijiensis. Black sigatoka is the more economically devastating, causing causes significant reductions in leaf area, yield losses of 50% or more, and premature ripening, a serious defect in exported fruit. It is more damaging and difficult to control than the related yellow sigatoka disease, and has a wider host range that includes the plantains and dessert and ABB cooking bananas that are usually not affected by yellow sigatoka.

In export plantations, black sigatoka is controlled with frequent applications of fungicides. This is a very expensive practice because it includes the use of airplanes or helicopters, permanent landing strips and facilities for mixing and loading the fungicides, and the high recurring expense of the spray materials themselves. In total, it has been estimated that these costs are ultimately responsible for 25% of the final retail price of these fruit in the importing countries (www.scisoc.org/feature/banana/top.html as found on Apr. 17, 2000). Different sterol demethylation inhibitors (DMIs) are now the most commonly used compounds for the control of sigatoka, but increased tolerance of the pathogen to the DMI fungicides has made it necessary to increase applications in several countries in banana-growing regions to frequencies of 25–40 per year (www.scisoc.org/feature/banana/top.html as found on Apr. 17, 2000).

Although black sigatoka can often be recognized visually, unambiguous diagnosis can be complicated by the presence of other pathogens found on banana leaves. Isolation of the pathogen, which is most successfully achieved by ascospore discharge from necrotic leaf material, is often confounded by the absence of mature perithecia, and even when obtained in culture, I M. fijiensisand M. musicola are not readily visually differentiated (Johanson and Jeger Mycol. Res. 97 (6): 670–674 (1993)).

Biomedical researchers have used PCR-based techniques for some time and with moderate success to detect pathogens in infected animal tissues. More recently, however, this technique has been applied to detect plant pathogens. The presence of Gaumannomyces graminis in infected wheat has been detected using PCR of sequences specific to the pathogen mitochondrial genome (Schlesser et al., 1991; Applied and Environ. Microbiol. 57: 553–556), and random amplified polymorphic DNA (i.e. RAPD) markers were able to distinguish numerous races of Gremmeniella abietina, the causal agent of scleroderris canker in conifers. U.S. Pat. No. 5,585,238 (herein incorporated by reference in its entirety) describes primers derived from the ITS sequences of the ribosomal RNA gene region of strains of Septoria tritici, Septoria nodorum, Pseudocercosporella herpotrichoides (R- and W-types), Mycosphaerella fijiensis, and Mycosphaerella musicola and their use in the identification of these fungal isolates using PCR-based techniques. In addition, U.S. Pat. No. 5,955,274 (herein incorporated by reference in its entirety) describes primers derived from the ITS sequences of the ribosomal RNA gene region of strains of Fusarium and their use in the identification of these fungal isolates using PCR-based techniques. Furthermore, U.S. Pat. No. 5,800,997 (herein incorporated by reference in its entirety) describes primers derived from the ITS sequences of the ribosomal RNA gene region of strains of Cercospora, Helminthosporium, Kabatiella, and Puccinia and their use in the identification of these fungal isolates using PCR-based techniques.

In view of the above, there is a real need for the development of technology that will allow the identification of additional specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention pertains to methods of identification of different pathotypes of plant pathogenic fungi. The invention provides Internal Transcribed Spacer (ITS) DNA sequences that show variability between different fungal pathotypes. Such DNA sequences are useful in the method of the invention as they are used to derive primers for use in polymerase chain reaction (PCR)-based diagnostic assays. These primers generate unique fragments in PCR reactions in which the DNA template is provided by specific fungal pathotypes and is thus used to identify the presence or absence of specific pathotypes in host plant material before the onset of disease symptoms.

In particular, the present invention provides the Internal Transcribed Spacer (ITS) DNA sequences from a heretofore unknown species of Mycosphaerella, as well as ITS-derived diagnostic primers for the detection of this species of Mycosphaerella and for differentiating it from other Mycosphaerella species such as *Mycosphaerella fijiensis* and *Mycosphaerella musicola*.

In one embodiment, the present invention provides a DNA molecule isolated from the ribosomal RNA gene region of a fungal pathogen, wherein said DNA molecule is the Internal Transcribed Spacer (ITS) DNA sequence of a heretofore unknown species of Mycosphaerella. In a preferred embodiment, the Internal Transcribed Spacer sequence from the heretofore unknown species of Mycosphaerella is selected from the group consisting of: SEQ ID NO: 14, SEQ ID NO: 15, SEQ ID NO: 16, and SEQ ID NO: 19.

According to another embodiment, the present invention provides an oligonucleotide primer for use in PCR-based detection of a Mycosphaerella species, wherein said primer has sequence identity with at least 10 contiguous nucleotides of the Internal Transcribed Spacer sequence from the heretofore unknown species of Mycosphaerella. Preferably, said oligonucleotide primer has a nucleotide sequence consisting essentially of the sequence set forth in SEQ ID NO:5, 6, 7, 8, 9, 10, 11, 12, or 13. By "consisting essentially of" is meant up to 10 additional residues on either the 5' or 3' end, or both the 5' and 3' end, of SEQ ID NO:5, 6, 7, 8, 9, 10, 11, 12, or 13. Most preferably, the oligonucleotide primer is selected from the group consisting of SEQ ID NOs:5–13.

According to yet another embodiment, the present invention provides a pair of oligonucleotide primers for use in PCR-based detection of a Mycosphaerella species, wherein at least one of said primers is the oligonucleotide primer described in the preceding paragraph. Preferably, the pair of oligonucleotide primers is selected from the group consisting of: SEQ ID NO:5 and SEQ ID NO:10; SEQ ID NO:5 and SEQ ID NO:11; SEQ ID NO:5 and SEQ ID NO:12; SEQ ID NO:5 and SEQ ID NO:13; SEQ ID NO:5 and SEQ ID NO:4; SEQ ID NO:6 and SEQ ID NO:10; SEQ ID NO:6 and SEQ ID NO:11; SEQ ID NO:6 and SEQ ID NO:12; SEQ ID NO:6 and SEQ ID NO:13; SEQ ID NO:6 and SEQ ID NO:4; SEQ ID NO:7 and SEQ ID NO:10; SEQ ID NO:7 and SEQ ID NO:11; SEQ ID NO:7 and SEQ ID NO:12; SEQ ID NO:7 and SEQ ID NO:13; SEQ ID NO:7 and SEQ ID NO:4; SEQ ID NO:8 and SEQ ID NO:10; SEQ ID NO:8 and SEQ ID NO:11; SEQ ID NO:8 and SEQ ID NO:12; SEQ ID NO:8 and SEQ ID NO:13; SEQ ID NO:8 and SEQ ID NO:4; SEQ ID NO:9 and SEQ ID NO:10; SEQ ID NO:9 and SEQ ID NO:11; SEQ ID NO:9 and SEQ ID NO:12; SEQ ID NO:9 and SEQ ID NO:13; SEQ ID NO:9 and SEQ ID NO:4; SEQ ID NO:1 and SEQ ID NO:10; SEQ ID NO:1 and SEQ ID NO:11; SEQ ID NO:1 and SEQ ID NO:12; and SEQ ID NO:1 and SEQ ID NO:13. Most preferably, the pair of oligonucleotide primers is SEQ ID NO: 7 and SEQ ID NO: 12.

According to still another embodiment, the present invention provides a method for the detection of a Mycosphaerella species, comprising: (a) isolating DNA from plant tissue infected with said Mycosphaerella species; (b) amplifying a part of the Internal Transcribed Spacer sequence of said Mycosphaerella species using said DNA as a template in a polymerase chain reaction with a pair of the above-described primers; and (c) detecting said Mycosphaerella species by visualizing the amplified part of the Internal Transcribed Spacer sequence.

This invention provides the possibility of assessing potential damage in a specific crop variety-pathogen strain relationship and of utilizing judiciously the diverse armory of fungicides that is available. Furthermore, the invention can be used to provide detailed information on the development and spread of specific pathogen races over extended geographical areas. The invention provides a method of detection that is especially suitable for diseases with a long latent phase.

Kits useful in the practice of the invention are also provided. The kits find particular use in the identification of a Mycosphaerella fungal pathogen.

BRIEF DESCRIPTION OF THE SEQUENCES IN THE SEQUENCE LISTING

SEQ-ID-NO:1 Oligonucleotide Primer ITS1.
SEQ-ID-NO:2 Oligonucleotide Primer ITS2.
SEQ-ID-NO:3 Oligonucleotide Primer ITS3.
SEQ-ID-NO:4 Oligonucleotide Primer ITS4.
SEQ-ID-NO:5 Oligonucleotide Primer J-BP1.
SEQ-ID-NO:6 Oligonucleotide Primer J-BP2.
SEQ-ID-NO:7 Oligonucleotide Primer J-BP3.
SEQ-ID-NO:8 Oligonucleotide Primer J-BP4.
SEQ-ID-NO:9 Oligonucleotide Primer J-BP5.
SEQ-ID-NO:10 Oligonucleotide Primer J-BP6.
SEQ-ID-NO:11 Oligonucleotide Primer J-BP7.
SEQ-ID-NO:12 Oligonucleotide Primer J-BP8.
SEQ-ID-NO:13 Oligonucleotide Primer JB-473.
SEQ-ID-NO:14 Truncated DNA sequence for the Internal Transcribed Spacer of a fungus amplified from banana sample "Capesterre-babin 2" (pCRBPCapbabB2-1).
SEQ-ID-NO:15 Truncated DNA sequence for the Internal Transcribed Spacer of a fungus amplified from banana sample "Matouba bas 3" (pCRBPMatbasB3-2).
SEQ-ID-NO:16 Truncated DNA sequence for the Internal Transcribed Spacer of a fungus amplified from banana sample "Temoin Infest Forte" (pCRBPMf9).
SEQ-ID-NO:17 DNA sequence for the Internal Transcribed Spacer of *Mycosphaerella fijiensis* ATCC isolate #22116 (U.S. Pat. No. 5,585,238).
SEQ-ID-NO:18 DNA sequence for the Internal Transcribed Spacer of *Mycosphaerella musicola* ATCC isolate #22115 (U.S. Pat. No. 5,585,238).
SEQ-ID-NO:19 Consensus sequence of Internal Transcribed Spacer DNA of fungi amplified from three infected banana samples (Consensus of SEQ ID NOs: 14–16).

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include the Internal Transcribed Spacer (ITS) sequences of the ribosomal RNA gene region of a particular Mycosphaerella fungal pathogen as well as primers derived from this region that are capable of identifying this Mycosphaerella pathogen. ITS DNA sequences from different pathotypes within a pathogen species or genus, which vary between the different members of the species or genus, can be used to identify those specific members.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS1 and ITS2, of around 300 bp (White et al., 1990; In: PCR Protocols; Eds.: Innes et al.; pages 315–322). In addition, the transcriptional units are separated by non-transcribed spacer sequences (NTSs). ITS and NTS sequences are particularly suitable for the detection of specific pathotypes of different fungal pathogens.

The DNA sequences of the invention are from the Internal Transcribed Spacer sequences of the ribosomal RNA gene region of a heretofore unknown species of a Mycosphaerella plant pathogen. The ITS DNA sequences from different pathotypes within a pathogen species or genus vary among the different members of the species or genus. Once having determined the ITS sequences of a pathogen, these sequences can be aligned with other ITS sequences, such as those from *M. fijiensis* and *M. musicola*. In this manner, primers can be derived from the ITS sequences. That is, primers can be designed based on regions within the ITS sequences that contain the greatest differences in sequence among the fungal pathotypes. These sequences and primers based on these sequences can be used to identify specific pathogens.

Sequences of representative oligonucleotide primers derived from the Mycosphaerella ITS sequences of the invention are disclosed in SEQ ID NOs:5–13. The sequences find use in the PCR-based identification of the pathogens of interest.

Methods for the use of the primer sequences of the invention in PCR analysis are well known in the art. For example, see U.S. Pat. Nos. 4,683,195 and 4,683,202, as well as Schlesser et al. (1991) *Applied and Environ. Microbiol.* 57:553–556. See also, Nazar et al. (1991; *Physiol. and Molec. Plant Pathol.* 39: 1–11), which used PCR amplification to exploit differences in the ITS regions of *Verticillium albo-atrum* and *Verticillium dahliae* and therefore distinguish between the two species; and U.S. Pat. No. 5,585,238, which describes similar techniques to distinguish the banana pathogens *Mycosphaerella fijiensis* and *Mycospharella musicola*.

The ITS sequences are compared within each pathogen group to locate divergences that might be useful to test in PCR to distinguish the different species and/or strains. From the identification of divergences, numerous primers are synthesized and tested in PCR-amplification. Templates used for PCR-amplification testing are firstly purified pathogen DNA, and subsequently DNA isolated from infected host plant tissue. Thus, it is possible to identify pairs of primers that are diagnostic, i.e. that identify one particular pathogen species or strain but not another species or strain of the same pathogen. Primers are also designed to regions highly conserved among the species to develop genus-specific primers as well as primers that will identify any of several fungal pathogens that cause a particular disease. For example, as described herein, primers are developed to differentiate a heretofore unknown species of Mycosphaerella from other species of Mycosphaerella such as *M. fijiensis* and *M. musicola*.

Preferred primer combinations are able to distinguish between the different species or strains in infected host tissue, i.e. host tissue that has previously been infected with a specific pathogen species or strain. This invention provides numerous primer combinations that distinguish the heretofore unknown species of Mycosphaerella from other species of Mycosphaerella such as *M. fijiensis* and *M. musicola*. The primers of the invention are designed based on sequence differences among the fungal ITS regions. A minimum of one base pair difference between sequences can permit design of a discriminatory primer. Primers designed to a specific fungal DNA's ITS region can be used in combination with a primer made to a conserved sequence region within the ribosomal DNA's coding region to amplify species-specific PCR fragments. In general, primers should have a theoretical melting temperature between about 60° C. to about 70° C. to achieve good sensitivity and should be void of significant secondary structure and 3' overlaps between primer combinations. Primers generally have sequence identity with at least about 5–10 contiguous nucleotide bases of ITS1 or ITS2. In preferred embodiments, primers are anywhere from approximately 5 to 30 nucleotide bases long.

The present invention lends itself readily to the preparation of "kits" containing the elements necessary to carry out the process. Such a kit may comprise a carrier being compartmentalized to receive in close confinement therein one or more containers, such as tubes or vials. One of the containers may contain unlabeled or detectably labeled DNA primers. The labeled DNA primers may be present in lyophilized form or in an appropriate buffer as necessary. One or more containers may contain one or more enzymes or reagents to be utilized in PCR reactions. These enzymes may be present by themselves or in admixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show typical experimental protocols that can be used in the selection of suitable primer sequences, the testing of primers for selective and diagnostic efficacy, and the use of such primers for disease and fungal isolate detection. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor Laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Fungal Isolates and Genomic Fungal DNA Extraction

See Table 1 for a listing of the fungal isolates used and their source. Fungi are grown in 150 ml potato dextrose broth inoculated with mycelial fragments from PDA (Potato Dextrose Agar) cultures. Cultures are incubated on an orbital shaker at 28° C. for 7–11 days. Alternatively, mycelia are isolated directly from a PDA plate. Mycelia are pelleted by centrifugation and then ground in liquid nitrogen, and total genomic DNA is extracted using the protocol of Lee and Taylor (1990; In: *PCR Protocols: A Guide to Methods and Applications*; Eds.: Innes et al.; pages 282–287).

TABLE 1

Source of Test Isolates

| Isolate | Organism | Source | Isolation | Origin |
|---------|----------|--------|-----------|--------|
| 22116 | M. fijiensis | ATCC[1] | Banana | Philippines |
| 22115 | M. musicola | ATCC[1] | Banana | Philippines |
| 24046 | M. citri | ATCC[1] | Grapefruit | Florida |
| 62714 | M. graminicola | ATCC[1] | Wheat | Montana |
| 36054 | M. diformis | ATCC[1] | Banana | Honduras |
| PA92 | M. fijiensis | A. Johanson[2] | Banana | Panama |
| PNG291 | M. fijiensis | A. Johanson[2] | Banana | Papua New Guinea |
| GH6-3 | M. fijiensis | A. Johanson[2] | Banana | Ghana |
| TG120 | M. fijiensis | A. Johanson[2] | Banana | Tonga |
| HSB4 | M. fijiensis | A. Johanson[2] | Banana | Honduras |
| RT689 | M. fijiensis | A. Johanson[2] | Banana | Rarotonga (Cook Is.) |
| CR548 | M. musicola | A. Johanson[2] | Banana | Costa Rica |
| CI31 | M. musicola | A. Johanson[2] | Banana | Ivory Coast |
| CB90 | M. musicola | A. Johanson[2] | Banana | Colombia |
| BD1-4 | M. musae | A. Johanson[2] | Banana | Barbados |

[1]American Type Culture Collection, Rockville, Maryland, USA
[2]Dr. Andrea Johanson, Natural Resources Institute, UK Example 2

DNA Extraction from Banana Tissues

DNA is extracted from banana leaves using a modified version of the Rapid DNA Extraction Protocol from the MicroProbe Corporation's (Garden Grove, Calif.) IsoQuick Nucleic Acid Extraction Kit (cat#MXT-020-100) as follows:

(1) Approximately 0.2 g of tissue are cut from banana leaves with ethanol washed scissors and placed in sterile Eppendorf tubes.
(2) 50 μL of Sample Buffer A and 50 μL of (Reagent #1 Lysis Solution) are added to the tubes as well as a few grains of sand to help macerate the tissue.
(3) The tissue is ground until fibrous using a Kontes pestle.
(4) The sand and debris is separated from the supernatant containing liberated DNA by centrifuging the samples at 10,000×G for 5 minutes. The supernatant is transferred to a fresh Eppendorf tube.
(5) 50 μL of Reagent 2 (Extraction Matrix) is added to the supernatant.
(6) 200 μL of Reagent 3 (Extraction Buffer) is added to the mixture and the samples are vortexed.
(7) Samples are centrifuged at 12,000×G for 5 minutes. Approximately 200 μL of aqueous phase is transferred to a new tube.
(8) 0.1× the volume of aqueous phase of Reagent #4 (Sodium Acetate) is added to the aqueous phase.
(9) An equal volume of isopropanol is added and the mixture is vortexed.
(10) The DNA is spun down to a pellet at 12,000×G for 10 minutes.
(11) The isopropanol is poured off and 0.5 μL of ice-cold 70% ethanol is added.
(12) The wash is spun down at 12,000×G for 5 minutes.
(13) The DNA is resuspended in 50 μL of TE with 100 μg/mL RNase.

Samples of banana leaves with evidence of sigatoka are obtained from Martinique and Guadeloupe (Table 2). Visual disease assessments are made by looking for lesions on the banana leaf surface. DNA preparations are made from them using the protocol outlined in this example.

TABLE 2

Source of Banana Leaf Tissues

| Designation | Country of Origin | Visual Disease Assessment |
|-------------|-------------------|---------------------------|
| Capesterre-babin 2 | Guadeloupe | Infected |
| Matouba bas 3 | Guadeloupe | Infected |
| Temoin 0 | Guadeloupe | No Symptoms |
| Temoin Infeste Forte | Martinique | Infected |

Example 3

Polymerase Chain Reaction Amplification

Polymerase chain reactions are performed with the GeneAmp Kit from Perkin-Elmer (Foster City, Calif.; part no. N808-0009) using 50 mM KCl, 2.5 mM $MgCl_2$, 10 mM Tris-HCl, pH8.3, containing 200 μM of each dTTP, dATP, dCTP, and dGTP, 50 pmol each primer, 2.5 units of Taq polymerase and 10 ng of genomic DNA. Reactions are run for 30–40 cycles of 15 s at 94° C., 15 s at 50° C.–70° C., and 45 s at 72° C. in a Perkin-Elmer Model 9600 or 9700 thermal cycler. The products are analyzed by loading 10 μl of each PCR sample on a 1.0% agarose gel and electrophoresing.

Example 4

Synthesis and Purification of Oligonucleotides

Oligonucleotides (primers) are synthesized by, for example, either Integrated DNA Technologies (Coralville, Iowa) or Midland Certified Reagent Company (Midland, Tex.).

Example 5

Identification Of A Heretofore Unknown Mycosphaerella Species Infecting Bananas

The sequence amplified from infected banana leaves using primer JB473 (SEQ ID NO:13) and primer ITS4 (SEQ ID NO:4) in the polymerase chain reaction as described in Example 3 is sequenced for comparison with *M. fijiensis* and *M. musicola* ITS region sequences (SEQ ID NOs:17 and 18, respectively). Sequences (SEQ ID NOs:14, 15, and 16) are obtained for products amplified from infected banana leaves from three different sources. Because the three sequences share 99.5–100% homology, a consensus sequence representing all three is made (SEQ ID NO:19). The portion of this consensus sequence comprising ITS2 is compared to the GenBank public database to find similar sequences (BlastN 2.0.7, Altschul et al (1997), *Nucleic Acids Res.* 25:3389–3402). The ITS2 region of SEQ ID NO:19 blasts most closely to species of Mycosphaerella including *M. fijiensis, M. pini, M. africana*, and *M. keniensis* (Table 3).

TABLE 3

Closest Matches Found Among BlastN Results for the ITS2 Region of the Fungal DNA Consensus Sequence Amplified from Infected Banana Samples.

| GenBank Accession | Species | Score | E value |
| --- | --- | --- | --- |
| AF181705 | Mycosphaerella fijiensis | 167 | 1e-39 |
| AF211197.1 | Mycosphaerella pini | 147 | 1e-33 |
| AF173314.1 | Mycosphaerella africana | 147 | 1e-33 |
| AF173300.1 | Mycosphaerella keniensis | 147 | 1e-33 |

Example 6

Selection of Species-Specific Primers

A multiple sequence alignment is made of *M. fijiensis* and *M. musicola* ITS region sequences obtained from U.S. Pat. No. 5,585,238 (SEQ ID NOs:17 and 18, respectively) and the consensus sequence from the infected banana leaves (SEQ ID NO:19). The consensus sequence is found to share only 84–87% homology with those from *M. fijiensis* and *M. musicola*. Based on this evidence, we conclude that the sequence amplified using primers JB473 and ITS4 from infected banana leaves is neither from *M. fijiensis* nor from *M. musicola*, but rather from a heretofore unknown species of Mycosphaerella. Oligonucleotide primers that specifically target this novel sequence such as those shown below in Table 4 are synthesized according to Example 4 based on analysis of the aligned sequences. Primers are designed to the regions that contain the greatest differences in sequence among the fungal species.

In addition, the published ribosomal gene-specific primers ITS 1, ITS2, ITS3 and ITS4 (White et al., 1990; In: PCR Protocols; Eds.: Innes et al. pages 315–322) are synthesized for testing in combination with the primers specific for the ITS regions.

TABLE 4

Primers Designed for Detection of Novel Fungal Sequence

| Name | Oligo Sequence (5' → 3') | Identifier |
|---|---|---|
| J-BP1 | GCATCATTGCGTCGGAGTAA | SEQ ID NO:5 |
| J-BP2 | TCATTGCGTCGGAGTAAAAGT | SEQ ID NO:6 |
| J-BP3 | CATCATTGCGTCGGAGTAAAAG | SEQ ID NO:7 |
| J-BP4 | CATTGCGTCGGAGTAAAAGTGA | SEQ ID NO:8 |
| J-BP5 | GCGTCGGAGTAAAAGTGAATGA | SEQ ID NO:9 |
| J-BP6 | GCCTCCGAAGCGAATAGTTG | SEQ ID NO:10 |
| J-BP7 | GGCCTCCGAAGCGAATAGTT | SEQ ID NO:11 |
| J-BP8 | CCTCCGAAGCGAATAGTT | SEQ ID NO:12 |
| J-BP9 | GGCCTCCGAAGCGAATAG | SEQ ID NO:13 |

Example 6

Determination of Primer Specificity to Purified Fungal Genomic DNA

PCRs are performed according to Example 3 using different primer combinations (Table 5) in an attempt to amplify single specific fragments. Specific PCR amplification products are produced from primers designed from the ITS regions between the small and large ribosomal DNA subunits of each fungal strain of interest.

TABLE 5

Possible Combinations of ITS-Derived PCR Primers for the Specific Amplification of an Unknown Banana Pathogen.

| Target Organism | 5' primer | 3' primer | Approximate Size (bp) |
|---|---|---|---|
| *Mycosphaerella sp.* | J-BP1 (SEQ ID NO:5) | J-BP6 (SEQ ID NO:10) | 290 |
| *Mycosphaerella sp.* | J-BP1 (SEQ ID NO:5) | J-BP7 (SEQ ID NO:11) | 290 |
| *Mycosphaerella sp.* | J-BP1 (SEQ ID NO:5) | J-BP8 (SEQ ID NO:12) | 290 |
| *Mycosphaerella sp.* | J-BP1 (SEQ ID NO:5) | J-BP9 (SEQ ID NO:13) | 290 |
| *Mycosphaerella sp.* | J-BP1 (SEQ ID NO:5) | ITS4 (SEQ ID NO:4) | 380 |
| *Mycosphaerella sp.* | J-BP2 (SEQ ID NO:6) | J-BP6 (SEQ ID NO:10) | 290 |
| *Mycosphaerella sp.* | J-BP2 (SEQ ID NO:6) | J-BP7 (SEQ ID NO:11) | 290 |
| *Mycosphaerella sp.* | J-BP2 (SEQ ID NO:6) | J-BP8 (SEQ ID NO:12) | 290 |
| *Mycosphaerella sp.* | J-BP2 (SEQ ID NQ:6) | J-BP9 (SEQ ID NO:13) | 290 |
| *Mycosphaerella sp.* | J-BP2 (SEQ ID NO:6) | ITS4 (SEQ ID NO:4) | 380 |
| *Mycosphaerella sp.* | J-BP3 (SEQ ID NO:7) | J-BP6 (SEQ ID NO:10) | 290 |
| *Mycosphaerella sp.* | J-BP3 (SEQ ID NO:7) | J-BP7 (SEQ ID NO:11) | 290 |
| *Mycosphaerella sp.* | J-BP3 (SEQ ID NO:7) | J-BP8 (SEQ ID NO:12) | 290 |
| *Mycosphaerella sp.* | J-BP3 (SEQ ID NO:7) | J-BP9 (SEQ ID NO:13) | 290 |
| *Mycosphaerella sp.* | J-BP3 (SEQ ID NO:7) | ITS4 (SEQ ID NO:4) | 380 |
| *Mycosphaerella sp.* | J-BP4 (SEQ ID NO:8) | J-BP6 (SEQ ID NO:10) | 290 |
| *Mycosphaerella sp.* | J-BP4 (SEQ ID NO:8) | J-BP7 (SEQ ID NO:11) | 290 |
| *Mycosphaerella sp.* | J-BP4 (SEQ ID NO:8) | J-BP8 (SEQ ID NO:12) | 290 |
| *Mycosphaerella sp.* | J-BP4 (SEQ ID NO:8) | J-BP9 (SEQ ID NO:13) | 290 |
| *Mycosphaerella sp.* | J-BP4 (SEQ ID NO:8) | ITS4 (SEQ ID NO:4) | 380 |
| *Mycosphaerella sp.* | J-BP5 (SEQ ID NO:9) | J-BP6 (SEQ ID NO:10) | 290 |
| *Mycosphaerella sp.* | J-BP5 (SEQ ID NO:9) | J-BP7 (SEQ ID NO:11) | 290 |
| *Mycosphaerella sp.* | J-BP5 (SEQ ID NO:9) | J-BP8 (SEQ ID NO:12) | 290 |
| *Mycosphaerella sp.* | J-BP5 (SEQ ID NO:9) | J-BP9 (SEQ ID NO:13) | 290 |
| *Mycosphaerella sp.* | J-BP5 (SEQ ID NO:9) | ITS4 (SEQ ID NO:4) | 380 |
| *Mycosphaerella sp.* | ITS1 (SEQ ID NO:1) | J-BP6 (SEQ ID NO:10) | 420 |
| *Mycosphaerella sp.* | ITS1 (SEQ ID NO:1) | J-BP7 (SEQ ID NO:11) | 420 |
| *Mycosphaerella sp.* | ITS1 (SEQ ID NO:1) | J-BP8 (SEQ ID NO:12) | 420 |
| *Mycosphaerella sp.* | ITS1 (SEQ ID NO:1) | J-BP9 (SEQ ID NO:13) | 420 |

Example 7

Determination of Primer Specificity to Plant Tissue Infected with Fungi and Cross-Reactivity with Other Fungal Pathogens Total genomic DNA is isolated as described in Example 2 from visibly infected parts of banana leaves. PCRs are performed as described in Example 3 testing primer combinations such as those listed in Table 5 against DNA from the banana tissue. Purified fungal genomic DNAs are obtained as described in Example 1 and PCR assayed as described in Example 3 using the diagnostic primers. Other fungal DNA species and isolates are tested for the ability of the diagnostic primers to cross-react therewith. The results of representative experiments are as follows:

All primer combinations except for those involving primers ITS1 (SEQ ID NO:1) and ITS4 (SEQ ID NO:4) amplify a ~300 bp product from infected banana leaf extracts. Primers J-BP3 (SEQ ID NO:7) and J-BP8 (SEQ ID NO:12) appear to give the cleanest product. This pair is further tested against the panel of banana pathogens in Table 1. No cross-amplification is observed against these other fungal DNAs. When run against healthy banana tissue (Temoin 0 in Table 2) primer pair J-BP3/J-BP-8 gives no cross-amplification.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

What is claimed is:

1. A pair of oligonucleotide primers consisting of SEQ ID NO:7 and SEQ ID NO:12.

2. A method for the detection of a heretofore unknown Mycosphaerella species, comprising:
   (a) isolating DNA from plant tissue infected with said Mycosphaerella species;
   (b) amplifying a part of the Internal Transcribed Spacer sequence of said Mycosphaerella species using said DNA as a template in a polymerase chain reaction with a pair of primers according to claim 1; and
   (c) detecting said Mycosphaerella species by visualizing the amplified part of the Internal Transcribed Spacer sequence.

3. A diagnostic kit used in detecting a heretofore unknown Mycosphaerella species, comprising a pair of primers of claim 1.

* * * * *